United States Patent [19]

Cartwright et al.

[11] Patent Number: 5,292,659

[45] Date of Patent: Mar. 8, 1994

[54] **BIOLOGICALLY PURE PHYTOPATHOGENIC FUNGUS *COLLETOTRICHUM CAPSICI***

[76] Inventors: D. Kelly Cartwright, 408 Harlon Dr., Apt, A-2, Cary, N.C. 27511; George E. Templeton, II, 2310 Winwood Dr., Fayetteville, Ark. 72703

[21] Appl. No.: 828,850

[22] Filed: Jan. 31, 1992

[51] Int. Cl.$^5$ ............... C12N 1/14; C12P 1/02; A01N 63/00

[52] U.S. Cl. ............... 435/254.1; 435/171; 424/93 Q; 504/117

[58] Field of Search ............... 485/254; 435/171; 71/79; 424/93 Q

[56] References Cited

U.S. PATENT DOCUMENTS

| | | | |
|---|---|---|---|
| 3,849,104 | 11/1979 | Daniel et al. | 71/65 |
| 3,999,973 | 12/1976 | Templeton | 71/79 |
| 4,239,690 | 12/1980 | Gurusiddaiah et al. | 260/340.2 |
| 4,643,756 | 2/1987 | Cardina et al. | 71/79 |
| 4,808,207 | 2/1989 | Gotlieb et al. | 71/79 |
| 4,902,333 | 2/1990 | Quimby, Jr. | 71/79 |
| 5,028,253 | 7/1991 | Watson et al. | 71/79 |
| 5,034,328 | 7/1991 | Boyette | 435/254 |

OTHER PUBLICATIONS

McLean, K. S. et al., *Weeds as a Source of Colletotrichum copsici* . . . , 1991, 13(2):131–134. Abstract.

*Primary Examiner*—Douglas W. Robinson
*Assistant Examiner*—Deborah K. Ware
*Attorney, Agent, or Firm*—Allen E. Norris

[57] ABSTRACT

Control of pitted morningglory employing a phytopathogenic fungus *Colletotrichum capsici* Number NRRL 18944 or a mutation thereof.

2 Claims, No Drawings

BIOLOGICALLY PURE PHYTOPATHOGENIC FUNGUS *COLLETOTRICHUM CAPSICI*

FIELD OF THE INVENTION

The invention concerns a fungal pathogen *Colletotrichum capsici*, its use in a method for the control of pitted morningglory (*Ipomoea lacunosa* L.) and compositions containing it.

DESCRIPTION OF THE PRIOR ART

The use of biological control in combatting weeds has become increasingly attractive in recent years due most particularly to its advantages with respect to environmental impact.

*Colletotrichum gloeosporioides* f. sp. aeschynomene (Daniel et.al. U.S. Pat. No. 3,849,104) has been marketed commercially since 1982 for control of northern jointvetch in Arkansas rice fields. Chlamydospores of the fungus *Phytophthora palmivora* have been formulated for control of milkweed vine in Florida citrus groves (*Phytophthora palmivora*, Weed Science, W. H. Ridings, 1986, vol. 34, Suppl. 1, pp. 31-32). Unwanted persimmon trees in Oklahoma rangeland are controlled by hand inoculation with the wilt fungus *Acremonium diospyri* (C. A. Griffith, 1970 Samuel Roberts Noble Foundation, Inc., Ardmore, Okla.).

Other fungi with experimentally demonstrated potential for weed control include *Colletotrichum gloeosporioides* f. sp. malvae on round-leaved mallow (K. Mortensen, 1988, Weed Science, vol. 36, pp. 473-478 and CA Patent No. 1,276,798); *Colletotrichum coccodes* on velvetleaf (Wymore et.al., 1987, Weed Science, vol. 35, pp. 377-383) and on eastern black nightshade (Andersen et al., U.S. Pat. No. 4,715,881); *Colletotrichum malvarum* on prickly sida (Templeton, U.S. Pat. No. 3,999,973); *Alternaria cassiae* on sicklepod, showy crotalaria, and coffee senna (Walker, U.S. Pat. No. 4,390,360); *Fusarium lateritium* (Walker, U.S. Pat. No. 4,419,120); *Colletotrichum orbiculare* on spiny cocklebur (Auld, Australian Patent No. 602223); *Cercospora rodmanii* on waterhyacinth (Conway et. al. U.S. Patent No. 4,097,261); *Chondrostereum purpureum* on American blackcherry (de Jong et.al., 1990, Plant Disease, vol. 74, pp. 189-194); *Fusarium solani* f. sp. cucurbitae on Texas gourd (Weidemann and Templeton, 1988, Plant Disease, vol. 72, pp. 36-38); *Fusarium roseum* "Culmorum" on *Hydrilla verticillata* (Charudattan, U.S. Pat. No. 4,263,036); and *Alternaria euphorbiicola* on *Euphorbia heterophylla* L. (Riley, U.S. Pat. No. 4,871,386). A review of the use of microbials in weed control can be found in "Microbial Control of Weeds" Ed. David O. TeBeest, Chapman & Hall, NY (1991).

Pitted morningglory (*Ipomoea lacunosa* L.) is a serious and widespread weed in soybeans, cotton and peanuts throughout the southeastern United States ("Beware the pitted morningglory". Peanut Farmer, Specialized Agr. Pub. Raleigh N.C. 21(3):12; Elmore et. al. Proc. South. Weed Sci. Soc. 36:319-328 (1982); Riley et. al. Weed Sci. 36:663-666 (1988)) and elsewhere. It causes yield loss, increased lodging, seed quality degradation and difficulty with harvest. Control is difficult due to the weed's tolerance to many commonly used soil- and foliar-applied herbicides, its prolific growth habit and season long emergence (Eastman et. al. Proc. South. Weed Sci. Soc. 30:39-45 (1977); Murdock et. al. Weed Sci. 34:711-717 (1986); Rhodes et. al. Term. Farm. Home Sci. Spring 1987 21-24). There is therefore a need for alternative controls to replace or supplement existing methods.

Previous attempts to control morningglory species with fungi have been limited. Although there are a number of fungi reported from weedy Ipomoea species (Farr et al in Fungi on Plants and Plant Products in the United States. St. Paul, Minn. APS Press (1989)) most efforts have involved fungi which commonly incite common "rust" diseases (Templeton in *Biological Control of Weeds with Plant Pathogens*, Charudattan & Walker eds. NY John Wiley & Sons pp. 29-44 (1982)). Studies of fungi other than rusts include evaluation of a Colletotrichum sp. on ivyleaf morningglory (El-Wakil et. al. Proc. VI Int. Sym. on the Biol. Control of Weeds, Univ. of British Columbia, Vancouver, BC Delfosse ed. pp. 613-616) and *Fusarium oxysporum* Schlecht on smallflower morningglory (Crawford et. al. Plant Dis. 72:268 abst. 1988). *Colletotrichum dematium* f. sp. ipomoea has been reported on Tall morningglory (Grand, NC Agri. Res. Serv. Tech. Bull. 240) as has susceptibility of some morningglories to root pathogens of sweet potato (Clark et. al. Plant Dis. 67:907-909 (1983)). Within Colletotrichum species, *Colletotrichum capsici* (Syd.) Butler & Bisby has been reported on cotton (Roberts et. al. Phytopathology 74:390-397).

There are no known reports of Colletotrichum spp or other fungi for use in the control of pitted morningglory.

The present invention therefore concerns a novel strain of *Colletotrichum capsici* (Syd.) Butler & Bisby which is pathogenic on pitted morningglory and which at similar rates is innocuous to useful crops where pitted morningglory is a problem such as in soybean and cotton fields. (The strain according to the invention will be referred to hereinafter as "CPMG".)

SUMMARY OF THE INVENTION

The instant invention concerns a method for the control of pitted morningglory, which comprises applying to the weed or the locus thereof a plant growth controlling amount of the fungus CPMG or a fungus having the identifying characteristics thereof or a mutation thereof.

This invention differs from the prior art in that this fungus is a new pathogen of pitted morningglory with particular requirements for large scale production, formulation and application. This pathogen can be formulated as a spray using a wettable powder and various spreader/sticker or emulsion additives obvious to those skilled in the art. The invention therefore also concerns a plant growth controlling composition comprising a plant growth controlling amount of the fungus CPMG or a fungus having the identifying characteristics thereof or a mutation thereof in admixture with an agriculturally acceptable carrier or adjuvant as well as biologically pure cultures of the fungus CPMG or a fungus having the identifying characteristics thereof or a mutation thereof.

DETAILED DESCRIPTION OF THE INVENTION

Living specimens of CPMG according to the invention were deposited in the Patent Depository of the NRRL under the access number NRRL # 18944 on Jan. 29, 1992. The address of the NRRL is A. J. Lyons, Curator, ARS Patent Culture Collection (NRRL), Northern Regional Research Center, ARS, USDA, 1815 North University Street, Peoria, Ill. 61604 USA.

CPMG grows well and sporulates abundantly on a potato-dextrose agar supplemented with streptomycin sulfate (300 mg/ml) or chlortetracycline (12.5 mg/ml) (hereinafter PDA+ cf Tuite, Plant Pathological Methods; Burgess Publ. Co. Minneapolis, 1969).

In culture it forms dark, smooth, flat colonies with regular margins. It produces pink to orange conidial masses with numerous setae. Conidia grown on PDA+ are hyaline, falcate in shape and range in size from 16.8 to 26.4 microns long by 4 to 5.6 microns wide.

CPMG was originally isolated from diseased pitted morningglory seedlings along Beaver Lake (Benton/Carroll Counties, Arkansas). As mentioned above CPMG sporulates abundantly in culture on PDA+.

CPMG is restricted in host range and pitted morningglory and sharppod morningglory are the only plant species of the 37 tested which are susceptible to the pathogen which proved innocuous to lettuce, beet, sweet potato, soybean, cotton, rice, wheat, sweet corn and tomato at the rates tested. Consistent infection is achieved over a wide range of temperatures and inoculum concentrations with optimum weed mortality at 25°, 30° and 35° C.

CPMG grows well and sporulates on solid media and it is expected that it will be producible in submerged liquid culture.

CPMG may be used effectively as a mycoherbicide in diverse formulations, including agronomically acceptable adjuvants and carriers routinely utilized to facilitate dispersion of active ingredients over plant surfaces. Formulation, dosage, mode of application or other variables may affect mycoherbicide activity and will depend upon soil conditions, climate and other environmental considerations. The desired mode of application may warrant formulation in aqueous or non-aqueous media, as a dust, wettable powder, emulsifiable concentrate, granule or other type of formulation.

Examples of types of formulations which may be employed include those in U.S. Pat. application No. 07/641,224; U.S. Pat. No. 4,902,333; U.S. Pat. No. 5,074,902; U.S. Pat. No. 5,034,328; and U.S. Pat. No. 4,915,726 and Boyette et. al. in "Microbial Control of Weeds" TeBeest ed. Chapman & Hall NY 1991, pp 209-224, the contents of each of which, in this respect, is incorporated by reference.

In the control of pitted morningglory with CPMG the best results are obtained when the fungus infects plants at 25° and 30° with 24 hours dew with complete kill occurring after 5 to 7 days. Plants are also infected at 15°, 20°, 35°, however with mortality occurring only at 35°. A minimum dew period of greater than 12 hours appears necessary although split 12 hour dew periods resulted in satisfactory mortality. Complete control is achieved with inoculum concentrations of $5.5 \times 10^5$ to $5.5 \times 10^7$ conidia/ml at 30° C. with a 24 hour dew period.

CPMG may be combined with spores of other biological control agents or with chemical control agents in a comprehensive or broad-spectrum approach to pest control whereby application rates of chemicals employed would be expected to be equal to or less than those employed conventionally in some cases allowing control with otherwise sub-lethal rates of chemical. Examples of such chemical control agents include herbicides from the classes of triazines, diphenylethers, phenoxy- and benzoic acids, sulfonyl ureas and imidazolidones such as dicamba, 2,4-D, 2,4-DB, glyphosate, MCPP, dichlorprop, simazine, fluometuron, bromoxynil, oxyfluorfen, 2,3,6-TBA, trichlorpyr, naptalam, acifluorfen, metribuzin, lactofen, fomesafen, chlorimuron, imazaquin, norflurazon, etc. The choice of chemical control agent will of course depend on weed spectrum, compatibility with the fungus, and crop selectivity required. Applications of the fungus may also be made more than once during a growing season without the need for concern about run-off, drift or residue problems inherent to repeated chemical applications. The fungus is nontoxic to the applicator. The fungus might also be combined with other chemicals commonly used in farming operations, such as fertilizers, to minimize spray applications.

As used herein "plant growth controlling" is intended to mean the ability of the fungus according to the invention to infect its target plant *Ipomoea lacunosa* L. to a degree sufficient to reduce or prevent the ability of that weed to detrimentally affect the growth of the crop plants which it normally infests.

The invention also includes other fungi having the identifying characteristics of CPMG or being mutations thereof particularly those retaining the ability to infect and control the growth of *Ipomoea lacunosa* L.

The following examples illustrate the invention without in any way restricting the scope thereof.

EXAMPLE 1

In Vitro Methods a) Isolation The fungus is isolated from seedlings by rinsing sections of diseased tissue in a 0.5% NaOCl solution for 1 minute and placing them on potato dextrose agar supplemented with streptomycin sulfate (300 mg/ml) or chlortetracycline (12.5 mg/ml) (PDA+). Pure cultures are maintained on PDA+.

b) Stock Cultures Several isolates are screened for pathogenicity on pitted morningglory seedlings, and the most virulent selected for use in further tests. Conidia are collected from 8- to 11-day-old colonies grown on PDA+, placed in cryopreservative (1:1 solution of 40% glycerol:10% skim milk) contained in 1.5 ml plastic cryovials, and stored at −80° C. Aliquots from frozen stock cultures are utilized for increasing all inoculum.

c) Effect of temperature on conidia aermination and radial growth rate Germination of conidia is measured by spreading 0.1 ml of a suspension ($1 \times 10^6$ conidia/ml) onto PDA+ plates, wrapping the plates in foil, and incubating at 15°, 20°, 25°, 30° or 35° C. Germinated conidia are counted after 8 hours with a compound light microscope at 10X. One hundred conidia are counted per plate. A 5-mm plug taken from the margin of an actively growing colony of CPMG is placed mycelial side down in the center of a PDA+ plate, and the plates are wrapped in foil. Three replicate plates are incubated at 15°, 20°, 25°, 30° or 35° C. Colony diameter is measured after 4, 7 and 10 days. Experiments are repeated once. Best results are obtained at 30° and 25° C.

d) Inoculum production Conidia from the frozen stock tubes are streaked onto PDA+ plates and incubated on a laboratory bench under fluorescent lights (12-hour photoperiod) at room temperature. After 8 to 11 days, conidia are gently scraped from the colony surface with a microscope cover slip while rinsing with distilled water. The suspension is filtered through cheesecloth, quantified with a hemacytometer, and adjusted to the desired conidial concentration.

EXAMPLE 2

In Vivo Methods a) Plant Production Seeds from mature pitted morningglory plants are collected from naturally occurring field populations and stored at 12° C. Seedlings are obtained by planting seeds in commercial potting soil and vermiculite (3:1 v:v) in 7.6 cm diameter plastic pots. All plants for host range tests except sweet potato are grown from seed. Sweet potato cuttings are made from mature plants and rooted in water before potting. Plants are grown in a greenhouse under natural light until inoculation. Plants are watered daily and fertilized weekly (Peter's Fertilizer Products, Fogelsville, Pa. 18051). Pitted morningglory seedlings are thinned to 4 plants per pot immediately before inoculation.

b) Effect of dew period and dew temperature Pitted morningglory seedlings 3 to 5 days old are sprayed until runoff with 5 to $7\times10^6$ conidia/ml of CPMG using an aerosol atomizer (Sigma Chemical Company, St. Louis, Mo. 63178). Control plants are sprayed with distilled water. Seedlings are placed either in a controlled environmental growth chamber (Conviron, Model E-7, Pembina, N. Dak. 58271) maintained at 28°/24° C. (day/night) with a daily 14-hour photoperiod, or in a dew chamber (Percival Manufacturing Company, Model I-35D, Boone, Iowa 50036) in the dark at 100% RH periods of 6, 12, 18 or 24 hours at temperatures of 15°, 20°, 25°, 30° or 35° C. and then moved to the growth chamber. Noninoculated controls are maintained in the dew chamber for 24 hours. Seedlings in the growth chamber are monitored daily for disease development and mortality. After 10 days, plants are removed from pots, washed gently to remove soil from the roots, and air dried for 1 hour. Plants are separated by pot (replication), cut up, and weighed in aluminum weighing pans. After drying for 24 hours at 85° to 90° C. in a mechanical convection oven (Precision Scientific Group, Model 26, Chicago, Ill. 60647), the dry weight of both treated and control plants is recorded as a percentage of the highest dry weight value within each experiment. Optimum results are obtained at 25° and 30° C. with 24 hour of dew.

c) Effect of sequential dew periods on disease Pitted morningglory seedlings are inoculated and incubated for 12 hours in a 30° C. dew chamber in the dark, placed in a growth chamber for 12 hours of light, and then subjected to 12 additional hours of dew at 30° C. Inoculated seedlings held for single 12- or 24-hour dew periods are included as controls. After removal to a growth chamber, plant mortality is recorded after 10 days. Mortality rates of $>80\%$ are achieved.

d) Effect of inoculum concentration on disease Pitted morningglory seedlings are sprayed with conidial suspensions of $5.5\times10^3$ to $5.5\times10^7$ conidia/ml and held in a dew chamber for 24 hours at 30° C. Control plants are sprayed with distilled water. Plants are removed to a growth chamber, and mortality is recorded after 10 days.

Complete control is achieved with conidial concentration of $5.5\times10^5$ to $10^7$ conidial/ml at 24 hour dew and 30° C.

What is claimed is:

1. A biologically pure culture of a fungus having all of the identifying characteristics of *Colletotrichum capsici* NRRL 18944 or a mutation thereof.

2. A fungus according to claim 1 which is *Colletotrichum capsici* NRRL 18944.

* * * * *